United States Patent [19]
Marion et al.

[11] Patent Number: 5,965,145
[45] Date of Patent: Oct. 12, 1999

[54] USE OF HONEY AS KERATOLYTIC AGENT FOR IMPROVING THE RADIANCE AND THE COMPLEXION OF THE SKIN AND TREATING WRINKLES

[75] Inventors: Catherine Marion, Sceaux; Anne Vanstraceele, Paris, both of France

[73] Assignee: L'oreal, Paris, France

[21] Appl. No.: 08/901,522

[22] Filed: Jul. 28, 1997

[30] Foreign Application Priority Data

Jul. 26, 1996 [FR] France ................................. 96 09458

[51] Int. Cl.⁶ ...................................................... A61K 7/48
[52] U.S. Cl. ........................ 424/401; 514/844; 514/845; 514/846; 514/847; 514/557
[58] Field of Search ............................ 424/401; 514/844, 514/845, 846, 847, 557

[56] References Cited

FOREIGN PATENT DOCUMENTS

| 2 058 226 | 7/1971 | Germany . |
| 59-55809 | 3/1984 | Japan . |
| 6-38702 | 2/1994 | Japan . |
| 120673 | 12/1918 | United Kingdom . |

OTHER PUBLICATIONS

Derwent Publications Ltd., London, GB; AN 96–462975.
Derwent Publications Ltd., London, GB; AN 96–450917.
Karlsruhe, DE, Fichier Chemical Abstract, vol. 125, AN:308685.
Derwent Publications Ltd., London, GB; AN 95–200996.
Derwent Publications Ltd., London, GB; AN 95–194705.

*Primary Examiner*—Jyothsna Venkat
*Attorney, Agent, or Firm*—Oblon, Spivak, McClelland, Maier & Neustadt, P.C.

[57] ABSTRACT

A composition is described in which honey is the keratolytic agent in a cosmetic and/or dermatological composition, in particular as an active agent for improving the radiance of the complexion and/or for smoothing the skin of the face and/or body and/or for treating wrinkles and fine lines. The composition makes it possible to gently combat the ageing of the skin of the human face and/or body.

19 Claims, No Drawings

USE OF HONEY AS KERATOLYTIC AGENT FOR IMPROVING THE RADIANCE AND THE COMPLEXION OF THE SKIN AND TREATING WRINKLES

BACKGROUND OF THE INVENTION

1. Field of the Invention

The invention relates to a cosmetic or dermatological composition containing honey as a keratolytic agent and a method of applying same for improving the radiance of the complexion, smoothing the skin of the human face or body, or for treating wrinkles and fine lines. It also relates to a topical composition containing honey and at least one fatty alcohol. It relates also to a topical composition containing honey and at least one hydroxy acid, which composition is buffered at pH 5 and makes it possible to gently combat the ageing of the skin of the human face and/or body.

2. Discussion of the Background

There is an increasing desire by the population to look younger and less wrinkled by using cosmetic compositions containing active agents capable of combating ageing.

Unfortunately, conventional anti-ageing active ingredients, such as retinoids and acidic active agents, such as hydroxy acids, exhibit the major disadvantage of causing stinging, itching or tightness after they have been applied, which can result in great discomfort. Use of these compounds with sensitive skin is therefore often impossible.

To overcome the above disadvantages, attempts have been made to use hydroxy acids resulting from natural products, such as fruit or honey. Thus, the α-hydroxy acids extracted from honey are described as much less irritating than synthetic products (see Smith, Cosmetics & Toiletries, September 1994, vol. 109, p. 41–48). These acids are obtained by extraction from fermented honey. However, they still exhibit a degree of discomfort when applied to the skin.

The need consequently remains for a cosmetic and/or dermatological composition for combating ageing which does not exhibit the above-described disadvantages.

The inventors have found, surprisingly, that honey exhibits keratolytic properties and makes it possible to improve the radiance of the complexion of the skin and to smooth the features of the skin, thus causing the skin to appear younger and less wrinkled.

Honey has been used in cosmetic compositions intended for the treatment of ageing; see, for example, JP-A-59-55809, GB-A-120,673 and JP-A-6-38702. However, in these compositions, the honey is added as an additive to the active ingredients, which are active with respect to ageing, and its own effectiveness as keratolytic agent has never been described or realized.

SUMMARY OF THE INVENTION

One object of the present invention is consequently to provide a cosmetic composition and a method for improving the radiance of the complexion, for smoothing the skin, and for treating wrinkles and fine lines.

Another object of the invention is to provide a keratolytic agent for improving the radiance of the complexion, for smoothing the skin, and treating wrinkles and fine lines suitable for a dermatological composition.

Another object of the invention is a cosmetic and/or dermatological process for treating wrinkles, fine lines of the skin, and the visible signs of ageing.

Another object of the present invention is to gently combat the ageing or the visible signs of ageing of the skin of the human face or body using a keratolytic agent.

These and other objects of the present invention have been solved by a composition that contains honey as the keratolytic agent.

The first embodiment of the present invention is to provide a keratolytic composition including:
- a keratolytic effective amount of honey as the sole keratolytic effective agent; and
- a cosmetically acceptable medium.

The second embodiment of the present invention is to provide a keratolytic composition, including:
- a keratolytic effective amount of honey;
- at least one acidic active agent selected from the group consisting of α-hydroxy acid, β-hydroxy acid, α-keto acid, β-keto acid, and a mixture thereof;
- a pH buffered to about 5; and
- a cosmetically acceptable medium.

The third embodiment of the present invention is to provide a method for inducing keratolytic activity in skin, including:
applying to skin a composition including a keratolytic effective amount of honey.

The fourth embodiment of the present invention is to provide a method for treating wrinkles, fine lines, and the visible signs of ageing, including:
applying to skin a composition including a keratolytic effective amount of honey.

The fifth embodiment of the present invention is to provide a method for improving the radiance of the complexion, including:
applying to skin a composition including a keratolytic effective amount of honey.

DESCRIPTION OF THE PREFERRED EMBODIMENTS

Other features of the invention will become apparent in the course of the following descriptions of exemplary embodiments which are given for illustration of the invention and are not intended to be limiting thereof.

Honey is understood to mean an untreated honey, that is to say not fermented and not containing hydroxy acids, in contrast to the honey extract which is a fermentation product and which contains hydroxy acids.

The honey used according to the invention is preferably composed of a mixture of glucose, levulose, dextrin, sucrose, proteins and water, it being possible for the content of these various constituents to vary depending on the origin of the honey. Honey conventionally includes from 72 to 75% of the mixture of glucose and levulose, 15% water, 10% dextrin, 2.5% sucrose and 1% proteins.

The honey can have any origin. In particular, it can be an acacia honey, a lime honey, a mountain honey, a Gatinais's honey, an orange blossom honey or a honey derived from all kinds of flowers.

The amount of honey in the composition according to the invention must be in an effective amount so as to act as keratolytic agent and can range, for example, from 0.1 to 10%, preferably 0.1 to 5%, and more preferably from 0.1 to 2% of the total weight of the composition. These ranges include all values and subranges therebetween.

According to a specific embodiment of the invention, the composition contains, in addition to honey, at least one fatty alcohol which makes it possible to improve stability of the composition.

Use may in particular be made, as fatty alcohol, of cetyl alcohol and stearyl alcohol. The amount of fatty alcohol can range, for example, from 0.1 to 10% and preferably from 0.5 to 5% of the total weight of the composition. These ranges include all values and subranges therebetween.

Preferably, the present invention is a cosmetic or dermatological composition that contains, in a cosmetically and/or dermatologically acceptable medium, an effective amount of honey and at least one fatty alcohol.

Preferably, the composition contains, in addition to honey, one or a number of acidic active agent and a buffer of pH 5. This is because the inventors have found, surprisingly, that such a composition reduces the irritant effect of the acidic active agent without decreasing the activity of these active agents. The simultaneous presence of honey, of acidic active agent and of the buffer makes it possible to obtain a composition having a particularly satisfactory tolerance/effectiveness relationship.

Preferably, the present invention is consequently a cosmetic or dermatological composition containing, in a cosmetically and/or dermatologically acceptable medium, at least one acidic active agent that additionally contains honey and a buffer of pH 5.

Mention may in particular be made, as acidic active agents which can be used in the composition of the invention, of α-hydroxy acids or β-hydroxy acids, or a mixture thereof, which can be linear, branched or cyclic and saturated or unsaturated. Moreover, the hydrogen atoms of the carbon chain can be substituted by halogens or halogenated, alkyl, acyl, acyloxy, alkoxycarbonyl or alkoxy radicals having from 2 to 18 carbon atoms.

Mention may be made, as α-hydroxy acids, of glycolic, lactic, malic, tartaric, citric and mandelic acids. Mention may be made, as β-hydroxy acids, of salicylic acid and its acylated derivatives or 2-hydroxyalkanoic acids and their derivatives, 2-hydroxybenzoic acid and its derivatives such as 2-hydroxy-3-methylbenzoic acid and 2-hydroxy-3-methoxybenzoic acid.

Mention may in particular be made, as salicylic acid derivative, of those described in the documents FR-A-2,581, 542 and EP-A-3,378,936, the entire contents of which are hereby incorporated by reference, and in particular of 5-(n-octanoyl)salicylic, 5-(n-decanoyl)salicylic, 5-(n-dodecanoyl)salicylic, 5-(n-octyl)salicylic, 5-(n-heptyloxy) salicylic and 4-(n-heptyloxy)salicylic acids. It is also possible to use those described in the document EP-A-570, 230, the entire contents of which are hereby incorporated by reference.

It is also possible to use, as active agents α- or β-keto acids or a mixture thereof The amount of acidic active agent can range from 0.01 to 20% and preferably from 0.1 to 5% of the total weight of the composition. These ranges include all values and subranges therebetween.

To obtain the buffered composition according to the invention, its pH is adjusted to 5, or about 5, using bases, such as sodium hydroxide or triethanolamine, and then the buffer of pH 5 is added.

The buffer present in the composition according to the invention is not particularly limited, but can be in particular a citrate buffer of pH 5. The amount of buffer present in the composition can range, for example, from 0.1 to 10% and preferably from 0.5 to 3% of the total weight of the composition. These ranges include all values and subranges therebetween.

The composition defined above is capable of treating the skin gently, that is to say of improving the radiance of the complexion, of smoothing the skin and of treating wrinkles and/or fine lines of the skin. A further object of the present invention is consequently the cosmetic use of the compositions defined above for improving the radiance of the complexion and/or for smoothing the skin and/or treating wrinkles and fine lines of the skin.

Preferably, the composition of the invention containing honey includes a cosmetically and/or dermatologically acceptable medium, that is to say compatible with the skin, the scalp and the hair. It can be provided in all the pharmaceutical dosage forms normally used for a topical application, in particular in the form of an aqueous, aqueous/alcoholic or oily solution, of an oil-in-water or water-in-oil or multiple emulsion, of an aqueous or oily gel, of a liquid, pasty or solid anhydrous product or of a dispersion of oil in an aqueous phase with the use of spherules, it being possible for these spherules to be polymeric nanoparticles, such as nanospheres and nanocapsules, or better still lipid vesicles of ionic and/or non-ionic type.

This composition can be more or less fluid and have the appearance of a white or coloured cream, of an ointment, of a milk, of a lotion, of a serum, of a paste or of a foam. It can optionally be applied on the skin in the aerosol form. It can also be provided in the solid form and, for example, in the stick form. It can be used as care product, as cleansing product or alternatively as make-up product.

Preferably, the composition of the invention can also contain adjuvants generally known in the cosmetic and dermatological fields, such as hydrophilic or lipophilic gelling agents, hydrophilic or lipophilic active principles, preservatives, antioxidants, solvents, fragrances, fillers, screening agents, pigments, chelating agents, odour absorbers and colouring materials. The amounts of these various adjuvants are those conventionally used in the fields under consideration and, for example, from 0.01 to 20% of the total weight of the composition, preferably 0.1 to 20%, more preferably 1 to 10%, and most preferably 2 to 5% by weight of the composition. These ranges include all values and subranges therebetween. These adjuvants, depending on their nature, can be introduced into the fatty phase, into the aqueous phase, into the lipid vesicles and/or into the nanoparticles.

When the composition of the invention is an emulsion, the proportion of the fatty phase can range from 5 to 80% by weight and preferably from 5 to 50% of the total weight of the composition. The oils, the emulsifiers and the coemulsifiers used in the composition in the emulsion form are chosen from those conventionally used in the field under consideration. The emulsifier and the coemulsifier are present in the composition in a proportion ranging from 0.3 to 30% by weight and preferably from 0.5 to 20% of the total weight of the composition. The above ranges include all values and subranges therebetween.

Preferably, as oils which can be used in the invention, are mineral oils, oils of plant origin (apricot oil, sunflower oil), oils of animal origin, synthetic oils, silicone oils (cyclomethicone) and fluorinated oils (perfluoropolyethers). Use may also be made, as fatty substances, of fatty alcohols (cetyl alcohol), fatty acids or waxes (beeswax).

Preferably, as emulsifiers and coemulsifiers which can be used in the invention, for example, are esters of fatty acid and of polyethylene glycol, such as PEG-40 stearate or PEG-100 stearate, or esters of fatty acid and of polyol, such as glyceryl stearate and sorbitan tristearate.

Preferably, as hydrophilic gelling agents, are carboxyvinyl (carbomer) polymers, acrylic copolymers, such as acrylate/alkyl acrylate copolymers, polyacrylamides, polysaccharides, natural gums and clays and mention may be made, as lipophilic gelling agents, of modified clays, such as bentones, metal salts of fatty acids, hydrophobic silica and polyethylenes.

Preferably, as active agents, are moisturizers, such as polyols (for example glycerol), vitamins (for example D-panthenol), anti-inflammatory agents, soothing agents (allantoin, cornflower water), UVA and UVB screening agents, mattifying agents (for example the partially crosslinked polydimethylorganosiloxanes sold under the name KSG by Shin Etsu), and their mixtures.

It is also possible to add anti-wrinkle active agents other than honey, and preferably tensioning products such as plant proteins and their hydrolysates, more preferably the soya protein extract sold under the name of Eleseryl by the company LSN or the oats derivative sold under the name "Reductine" by the company Silab.

EXAMPLES

Having generally described this invention, a further understanding can be obtained by reference to certain specific examples which are provided herein for purposes of illustration and are not intended to be limiting unless otherwise specified. The proportions are given as percentage by weight.

Example 1

Cream for the Face

| Oily phase: | |
|---|---|
| Mineral oil | 15% |
| Cetyl alcohol | 4% |
| Glyceryl stearate | 3% |
| PEG-40 stearate | 2% |
| Sorbitan tristearate | 0.9% |
| Aqueous phase: | |
| Glycerol | 3% |
| Honey | 2% |
| Demineralized water | q.s. for 100% |

Procedure:

The aqueous and oily phases are heated separately to 70–80° C. The oily phase is then introduced into the aqueous phase at 65° C. with stirring. The emulsion is cooled to room temperature while continuing to stir.

A white cream is obtained which is capable of restoring radiance to the skin of the face.

In order to evaluate the keratolytic effect of this cream, a test was carried out in vivo on a panel of 18 women aged from 35 to 50 years who have dry skins. 2 mg/cm$^2$ of cream are applied on the inner face of the forearm of each subject and, 24 hours after application, the desquamation cells released are counted by cytofluorimetry. The operation is repeated 4 days in succession and all the cells released are counted. The test was carried out in parallel for an identical cream containing 5% of fruit acids (lactic acid, glycolic acid, citric acid and malic acid).

The results show that the keratolytic effect of the cream according to the invention is equivalent to that obtained with the cream containing the fruit acids. In addition, the cream according to the invention has the advantage of being less irritating than the creams containing acidic active agents, although as effective.

Example 2

Fluid for the Face

| Oily phase: | |
|---|---|
| Mineral Oil | 5% |
| Cetyl alcohol | 0.4% |
| Glyceryl stearate/PEG-100 stearate (Arlacel 165 sold by the company ICI) | 1.6% |
| Aqueous phase: | |
| Glycerol | 5% |
| Carbomer | 0.5% |
| Sodium hydroxide | 0.2% |
| Honey | 2% |
| Demineralized water | q.s. for 100% |

Procedure:

The oily phase is melted at 75° C. and the aqueous phase is heated to 80° C. The emulsion is then prepared by introducing the oily phase into the aqueous phase at 75° C. with stirring. The mixture is cooled to room temperature while continuing to stir.

The daily use of this fluid on the face makes it possible to regain a more luminous complexion and a smoother skin.

A test of effectiveness of this cream was carried out on a panel of 30 women. These women applied the cream on the face once a day for five days. 96% of the users found that the cream was very comfortable, even after applying for five days. Moreover, after the five days of use, 69% of the users found that they had a better appearance, 62% that their complexion was less muddy and 69% that they had a smoother skin.

Example 3

Cream for the Face

| Oily phase: | |
|---|---|
| Cetyl alcohol | 4% |
| Mineral oil | 15% |
| Glyceryl stearate | 3% |
| PEG-40 stearate | 2% |
| Sorbitan tristearate | 0.9% |
| Aqueous phase: | |
| Sodium hydroxide | 0.4% |
| Glycerol | 3% |
| Sodium citrate (buffer) | 1% |
| Fruit acids (lactic acid, glycolic acid, citric acid and malic acid) | 1% |
| Honey | 2% |
| Demineralized water | q.s. for 100% |

The procedure followed for the preparation of this cream is the same as in Example 1.

A test of effectiveness of this cream was carried out on a panel of 60 women who have sensitive skins. These women applied the cream on the face once a day for five weeks. At the end of this application period, 78% of the users were found to be satisfied with the product, 47% noticed an effect of radiance of the complexion and 56% found that they had a smoother skin.

Moreover, used in comparison with a product containing 2% of a mixture of fruit acids, this cream was judged as effective and less irritating.

Example 4
Fluid for the Face

| | |
|---|---|
| Oily phase | |
| Mineral oil | 5% |
| Cetyl alcohol | 0.4% |
| Glyceryl stearate/PEG-100 stearate | 1.6% |
| (Arlacel 165) | |
| Aqueous phase: | |
| Carbomer | 0.5% |
| Glycerol | 3% |
| Fruit acids (lactic acid, glycolic acid, citric acid and malic acid) | 1% |
| Sodium hydroxide | 0.4% |
| Citrate buffer | 3% |
| Honey | 1% |
| Demineralized water | q.s. for 100% |

The procedure followed for the preparation of this fluid is the same as in Example 2. The test of effectiveness of this fluid was carried out on a panel of 60 women who have sensitive skins. These women applied the fluid on the face once a day for five weeks. At the end of this application period, 59% of the users were found to be satisfied with the product, 56% noticed an effect of radiance of the complexion and 62% found that they had a smoother skin.

Moreover, this fluid was judged as effective as a product containing 1.4% of a mixture of fruit acids, while being less irritating.

Example 5
Two-Phase Lotion

| | |
|---|---|
| Oily phase | |
| Mineral oil | 8.75% |
| Cyclomethicone | 10% |
| Apricot oil | 6.25% |
| Aqueous phase: | |
| Glycerol | 3.75% |
| Honey | 0.75% |
| Preservatives | q.s. |
| Demineralized water | q.s. for 100% |

Procedure:

The aqueous phase is heated to 80° C. in order to dissolve the preservatives; mixing is carried out and then the mixture is cooled to room temperature. The oily phase is prepared at room temperature. The two phases are mixed and homogenized.

A two-phase lotion is obtained which is shaken before use and which, at rest, again separates into two phases. This lotion, on daily application on the face, makes it possible to regain a radiant complexion.

Example 6
Tonic Lotion

| | |
|---|---|
| Cornflour water | 5% |
| D-Panthenol | 0.2% |
| Honey | 0.5% |
| Preservatives | q.s. |
| Demineralized water | q.s. for 100% |

Procedure:

The preservatives are heated in water at 80° C. in order to dissolve them. The other constituents are then added. The combined constituents are mixed well. A transparent lotion is obtained which has toning and regenerating properties.

Example 7
Two-Phase Lotion

| | |
|---|---|
| Oily phase: | |
| Mineral oil | 10% |
| Cyclomethicone | 8.75% |
| Sunflower oil | 6.25% |
| Aqueous phase: | |
| Glycerol | 6% |
| Fruit acids (lactic acid, glycolic acid, citric acid and malic acid) | 0.375% |
| Sodium hydroxide | 0.15% |
| Honey | 1.5% |
| Citrate buffer | 0.75% |
| Preservatives | q.s. |
| Demineralized water | q.s. for 100% |

The procedure followed for the preparation of this lotion is the same as in Example 5.

Example 8
Tonic Lotion

| | |
|---|---|
| Allantoin | 0.1% |
| Fruit acids (lactic acid, glycolic acid, citric acid and malic acid) | 1% |
| Triethanolamine | 0.8% |
| Citrate buffer | 3% |
| Honey | 1% |
| Preservatives | q.s. |
| Demineralized water | q.s. for 100% |

The procedure followed for the preparation of this lotion is the same as in Example 6.

This application is based upon French Patent Application 96-09458, filed Jul. 26, 1996, the entire contents of which are hereby incorporated by reference.

What is claimed as new and is desired to be secured by Letters Patent of the United States is:

1. A composition comprising:
   0.1–10 weight percent honey;
   0.1–10 weight percent of a fatty alcohol selected from the group consisting of cetyl alcohol and stearyl alcohol
   0.01–20 weight percent of at least one acidic acid agent selected from the group consisting of glycolic, lactic, malic, tartaric, citric, mandelic, salicylic, 2-hydroxy-3-methyl benzoic, 2-hydroxy-3-methoxybenzoic, 5-(n-octanoyl)salicylic, 5-(n-decanoyl)salicylic, 5-(n-dodecanoyl)salicylic, 5-(n-octyl)salicylic, 5-(n-heptyloxy)salicylic and 4-(n-heptyloxy)salicylic acids;
   a pH buffed to about 5; and
   optionally 0.3–30 weight percent of an emulsifier or coemulsifier selected from the group consisting of PEG-40 stearate, PEG-100 stearate, glyceryl stearate and sorbitan tristearate.

2. The composition according to claim 1, wherein said honey comprises a mixture of glucose, levulose, dextrin, sucrose, proteins, and water.

3. The composition as claimed in claim 1, comprising a compound selected from the group consisting of PEG-40 stearate, PEG-100 stearate, glyceryl stearate and sorbitan tristearate.

4. The composition as claimed in claim 1, wherein the pH of the composition is 5.

5. The composition as claimed in claim 3, wherein the pH of the composition is 5.

6. The composition as claimed in claim 1, wherein said at least one acidic acid agent is salicylic acid.

7. The composition as claimed in claim 1, comprising at least one of 5-(n-octanoyl)salicylic, 5-(n-decanoyl)salicylic, 5-(n-dodecanoyl)salicylic, 5-(n-octyl)salicylic, 5-(n-heptyloxy)salicylic and 4-(n-heptyloxy)salicylic acids.

8. A method for inducing keratolytic activity in skin, comprising applying to skin the composition of claim 1.

9. A method for inducing keratolytic activity in skin, comprising applying to skin the composition of claim 2.

10. A method for inducing keratolytic activity in skin, comprising applying to skin the composition of claim 4.

11. A method for inducing keratolytic activity in skin, comprising applying to skin the composition of claim 5.

12. A method for inducing keratolytic activity in skin, comprising applying to skin the composition of claim 6.

13. A method for inducing keratolytic activity in skin, comprising applying to skin the composition of claim 1.

14. A method for improving the radiance of the complexion, comprising applying to skin the composition as claimed in claim 1.

15. A method for improving the radiance of the complexion, comprising applying to skin the composition as claimed in claim 3.

16. A method for improving the radiance of the complexion, comprising applying to skin the composition as claimed in claim 4.

17. A method for improving the radiance of the complexion, comprising applying to skin the composition as claimed in claim 5.

18. A method for improving the radiance of the complexion, comprising applying to skin the composition as claimed in claim 6.

19. A method for improving the radiance of the complexion, comprising applying to skin the composition as claimed in claim 7.

* * * * *